United States Patent [19] [11] Patent Number: 4,950,283
Dzubow et al. [45] Date of Patent: Aug. 21, 1990

[54] SURGICAL CLIP

[75] Inventors: Leonard M. Dzubow, Bryn Mawr; Allan E. Wulc, Rydel, both of Pa.; Paul Weber, Fort Lauderdale, Fla.

[73] Assignees: John Lezdey; Paul Weber, both of Philadelphia, Pa.

[21] Appl. No.: 291,774

[22] Filed: Dec. 29, 1988

[51] Int. Cl.⁵ .............................................. A61B 17/00
[52] U.S. Cl. ...................................... 606/216; 128/20
[58] Field of Search .............. 128/334 R, 20; 606/216

[56] References Cited

U.S. PATENT DOCUMENTS 4,177,802  12/1979  Ogami ..................................... 128/20
4,753,237  6/1988  Puchy ..................................... 128/335

FOREIGN PATENT DOCUMENTS 471440  10/1914  France ................................. 128/335

Primary Examiner—Randall L. Green
Assistant Examiner—Gary Jackson
Attorney, Agent, or Firm—John Lezdey

[57] ABSTRACT

A surgical clip for maintaining tension on a suture of a patient which comprises a spring member, a pair of opposing holding means at each end of the spring means for holding tied ends of the suture whereby the suture is continuously maintained under tension.

3 Claims, 1 Drawing Sheet

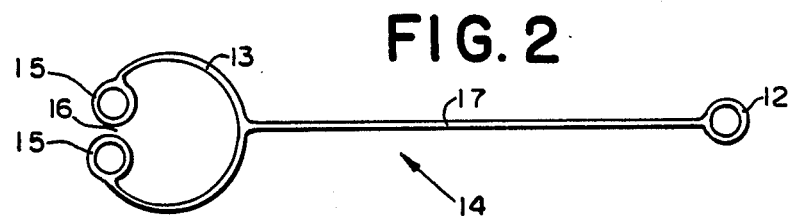
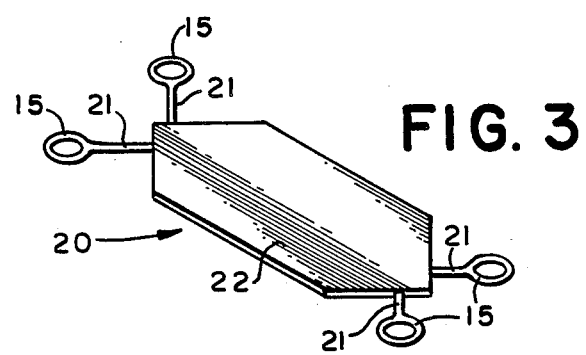
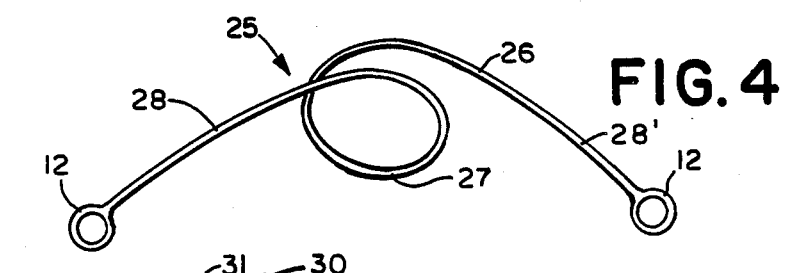
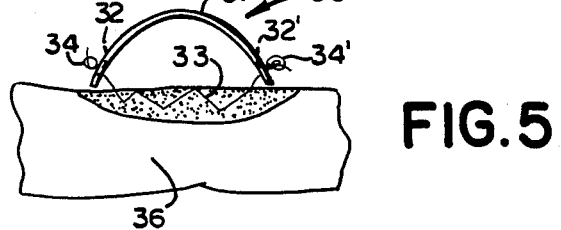
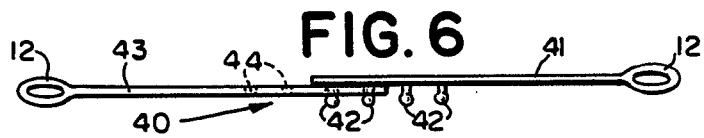

4,950,283

SURGICAL CLIP

FIELD OF THE INVENTION

The present invention relates to surgical clips which maintain tension of sutures or ligatures. More specifically, the invention is concerned with a running stitch tensor. The tensor maintains a tension on the suture so as to keep a wound closed so as to permit healing with little or reduced scarring.

BACKGROUND OF THE INVENTION

There are numerous disadvantages to performing conventional suture surgery. Buried sutures require additional surgical time to place, may eventuate in suture granulomas, may provide a nidus for infection, and may "spit". On the surface, nonabsorbable simple interrupted or running sutures placed into the trunk or extremities are usually left in place for two weeks. These nonabsorbable sutures unfortunately may result in pruritus, swelling of the immediately adjacent tissue, and unsightly "tracking". In addition, sudden impacts or other momentous forces may break the stitches or the intervening skin.

Additionally, other problems which occur with patients having sutures are opening of wounds because of body movement and failure to maintain sufficient tension on the sutures in the direction of stitching. At the present time, there are no means available for maintaining tension on sutures which will permit a patient to continue normal activity without loosening of sutures or spreading of the wound area. It has been found that when wounds are maintained in a tightly closed position for long periods of time, there is little scarring and an improvement in the healing process.

It is therefore an object of the invention to provide a surgical clip for continuously maintaining a running stitch under tension.

It is a further object of the invention to provide a tension on sutures during body movement.

SUMMARY OF THE INVENTION

The objects and advantages of the present invention can be achieved by providing a surgical clip for maintaining tension on a suture of a patient. The clip comprises a spring member having opposing end holding means.

The spring member comprises a flexible plate, bar, rod, wire or the like which may be flexed or bent so as to provide a continuous tension on the suture. That is, the spring member may be metallic such as steel, steel alloys, chromium alloys, etc. or a flexible plastic.

The end holding means advantageously comprises at least one ring-shaped member, a split ring member, a V-shaped member, a fork-shaped member, or the like which is capable of holding a knot. The knot which is made is either formed by tying the suture directly on the end of the holding means or formed of a size that prevents the knot from passing through the holding means.

The exposed ends of the open holding means may be provided with means for aiding insertion of a suture through the opening and/or preventing accidental puncturing of the patient.

Other objects and a fuller understanding of the invention will be had by referring to the following description and claims of a preferred embodiment, taken in conjunction with the accompanying drawings, wherein like reference characters refer to similar parts throughout the several views.

BRIEF DESCRIPTION OF THE DRAWING(S)

FIG. 1 is a top view of one type of surgical clip of the invention.

FIG. 2 is a top view of a surgical clip similar to FIG. 1 with one split ring;

FIG. 3 is a perspective view of a surgical clip with a plate spring member;

FIG. 4 is a side view of a further type of surgical clip;

FIG. 5 is a bar type surgical clip as placed on a wound; and,

FIG. 6 is a perspective view of an extensible surgical clip of the invention.

DESCRIPTION OF THE PREFERRED EMBODIMENT OF THE INVENTION

Although specific terms are used in the following description for the sake of clarity, these terms are intended to refer only to the particular structure of the invention selected for illustration in the drawings, and are not intended to define or limit the scope of the invention.

In accordance with one embodiment of the invention, there is provided a surgical clip 10 comprising a flexible metallic bar 11 having a ring-shaped holding means 12 at each end of the bar 11. The clip 10 may be utilized by tying one end of a suture to one of the ends 12, bending the bar 11 and knotting the suture so that the knot does not pass through. While in the bent condition, the clip 10 maintains constant tension on the suture.

As seen in FIG. 2, there may be provided a clip 14 comprising a rod 17 having a ring member 12 at one end and a split ring 13 at the other end. Advantageously, a pair of rounded means 15 is provided through which a suture to be inserted through the opening 16 and the knotted end to be held.

In FIG. 3 there is shown a surgical clip 20 comprising a plate 22 having V-shaped end members 21. The members 21 preferably contain at the end portions rounded means 15 so as to prevent accidental puncturing. A suture is held under tension by bending the plate 22 into an arc and capturing the knotted ends of a suture within the V-shaped members 21.

In FIG. 4 there is shown a surgical clip 25 comprising a wire 26 having a loop 27 and arms 28, 28' so as to provide the wire with bendability. At each end of the wire 26 are ring shaped holding means 12. The clip 25 functions by attaching one end a suture to one of the holding means 12, pinching the arms 28,28' together, and attaching the other end of the suture to the other end while maintaining tension.

In FIG. 5 there is shown a surgical clip 30 comprising a bar 31 used in connection with a suture 33 on a wound 36. The bar 31 has a pair of apertures 32,32' through which the ends 34,34' are knotted after the bar 31 is bent. The bent bar 31 maintains constant pressure on the suture during body movement.

FIG. 6 shows one form of an extensible clip 40. The clip 40 comprises a pair of arms 41,43 with end holding means 12 through which suture ends are inserted and knotted. The arm 43 is provided with a plurality of holes 44. Arm 41 is provided with a plurality of protrusions which can be inserted into the holes 44 to obtain a desired length. When the arms 41,43 are metallic, the protrusions 42 may be bent so as to permanently retain the protrusions 42 in the holes 44. When the members are plastic, deformation of the protrusions allows them to pass through the holes and expand into a retained position.

Prolene, a polypropylene, is the preferred suture for use with the invention since it is extremely inert and freely movable after weeks of placement.

OPERATION OF THE DEVICE

The device is used as follows, for example, on an elliptical defect. A suture tensor that is two to three cm longer than the defect's length is chosen. Buried absorbable suture may or may not be used in conjunction with the device. Another alternative is to use only one small buried absorbable stitch to conveniently narrow the defect. The far end of the suture is tied to one end of the tensor. The suture enters the skin through the end of the incision or it enters a distance from the incision. The traditional running subcuticular suture is placed along the wound. The needle of the suture then exits at the end of the wound or at a distance from the wound. The suture is pulled through the wound until the knot is about one half to one cm away from entering the skin. An assistant then bends or "activates" the device. The suture is passed through the loop while the device is bent. The tip of a hemostat clamps the suture just past the loop to hold the suture in place while a knot is tied to the loop.

This device may be used on the forehead, face, extremities and trunk. On sites below the neck, the device is left in place for three weeks, but may be left in place longer. Itching and scarring is minimal as compared with traditional suturing. The slight tenting which occurs along the suture line is beneficial since it soon flattens out, leaving a leval surface over the defect.

Although the invention has been described with a certain degree of particularity, it is understood that the present disclosure has been made only by way of example and that numerous changes in the details of construction and the combination and arrangement of parts may be resorted to without departing from the spirit and scope of the invention.

We claim:

1. A surgical clip attachment to a wound closing suture and for maintaining tension on the suture of a patient consisting of a spring means comprising a loop and two arms, and holding means at the end of each arm for holding tied ends of the suture whereby the suture is continuously and flexibly maintained under substantially even tension by means of said surgical clip outside of the wound.

2. The surgical clip of claim 1 wherein at least one holding means comprises a closed ring.

3. The surgical clip of claim 1 wherein said clip is metallic.

* * * * *